United States Patent [19]

Hueller

[11] Patent Number: 5,445,038
[45] Date of Patent: Aug. 29, 1995

[54] APPARATUS FOR SAMPLING FLUIDS IN CONTAINERS

[75] Inventor: Theodore H. Hueller, Cary, Ill.

[73] Assignee: Safety-Kleen Corp., Elgin, Ill.

[21] Appl. No.: 163,674

[22] Filed: Dec. 6, 1993

[51] Int. Cl.⁶ ............................................. G01N 1/12
[52] U.S. Cl. ........................... 73/864.63; 73/864.44; 73/864.45; 73/864.66; 73/864.74
[58] Field of Search ............ 73/864.44, 864.45, 864.63, 73/864.66, 864.73, 864.74

[56] References Cited

U.S. PATENT DOCUMENTS

| | | | |
|---|---|---|---|
| 408,223 | 8/1889 | Draper | 73/864.45 |
| 4,580,454 | 4/1986 | Deja | 73/864.63 |
| 5,031,469 | 7/1991 | Blackburn et al. | 73/864.63 |
| 5,113,711 | 5/1992 | Davloor et al. | 73/864.63 |

Primary Examiner—Richard E. Chilcot, Jr.
Assistant Examiner—Max H. Noori
Attorney, Agent, or Firm—James T. Fitzgibbon

[57] ABSTRACT

A liquid sampling apparatus comprising a sample retention tube, a tube plug, and an operating rod and handle unit. The retention tube is an open-ended cylinder made from a thin material. The plug includes a lower body portion with a skirt type seal, a rod-receiving center section, and tapered guide surfaces extending from the center toward the top of the body. The plug is secured to one end of an operating rod, and the other end of the rod has a handle in the form of a loop and a transverse section. The rod handle configuration enables the plug to be positively located in one of two desired positions.

10 Claims, 2 Drawing Sheets

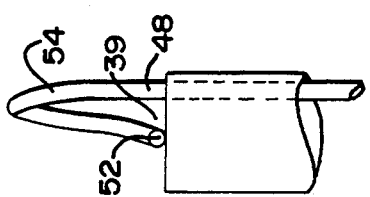
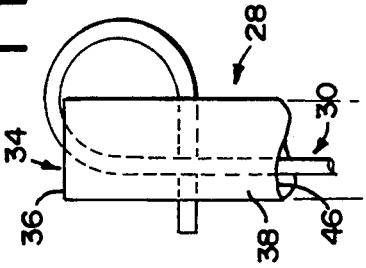
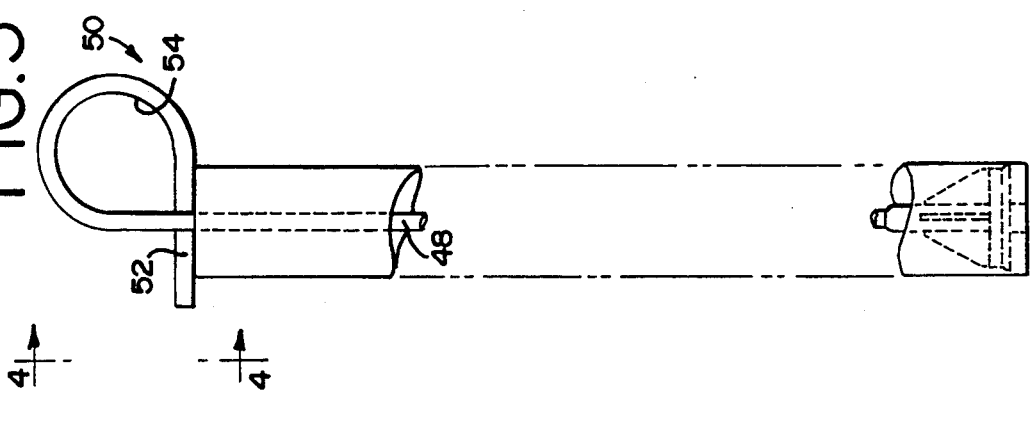
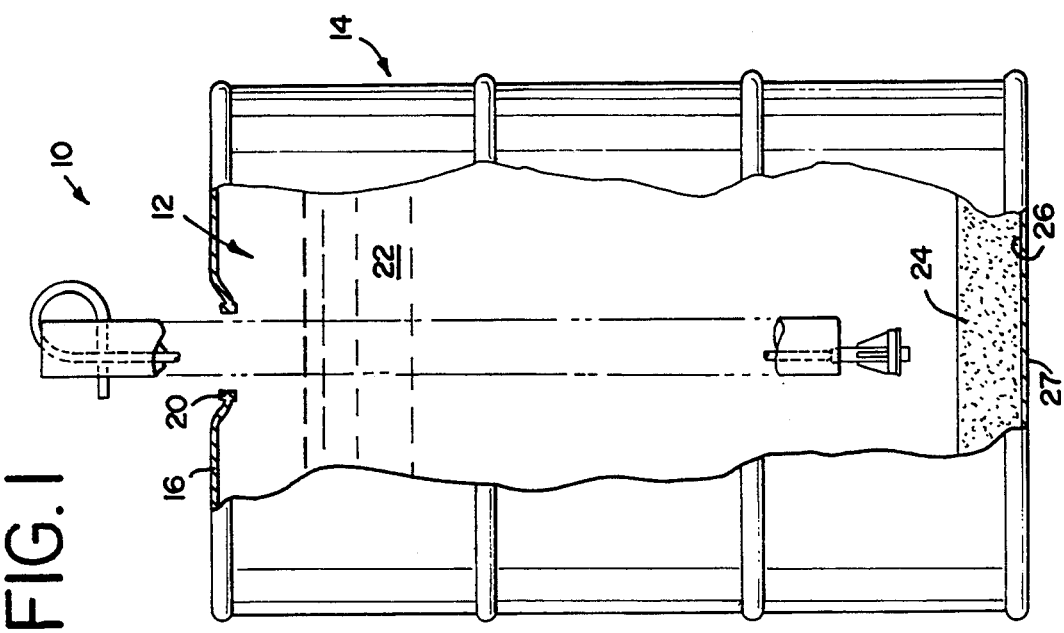

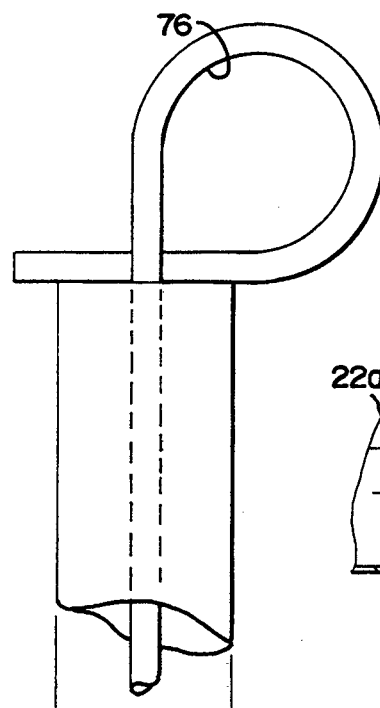
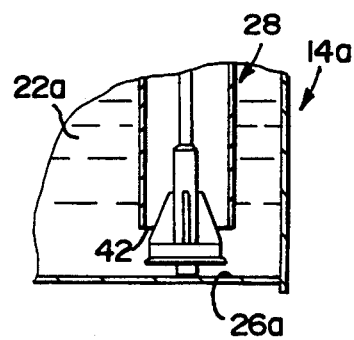
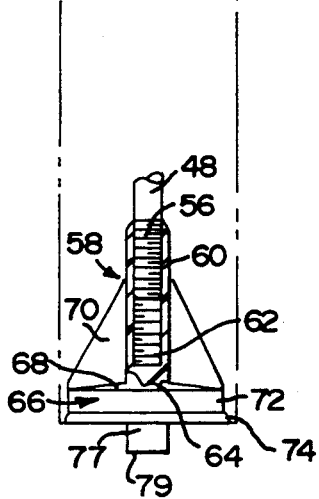
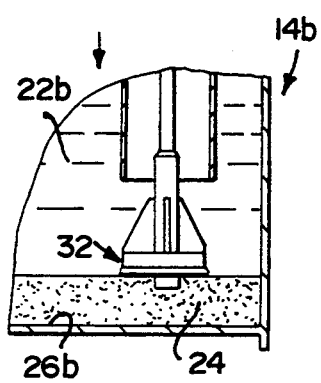
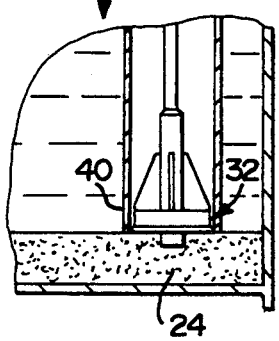
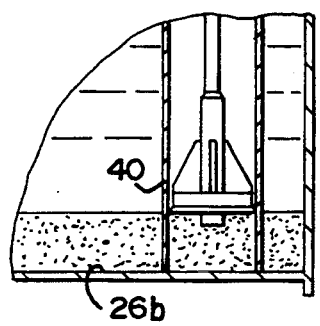

APPARATUS FOR SAMPLING FLUIDS IN CONTAINERS

BACKGROUND OF THE INVENTION

The present invention relates generally to sampling devices, and more particularly, to sampling devices that are constructed, arranged, and made with such materials that the devices may economically be thrown away after a single use, or after only a few uses. The products to be sampled are liquids in containers, including liquids that may have one or more layers of sludge or sediment at the bottom of the liquid.

In recent years, there has been growing concern from the standpoint of environmental protection with disposition of industrial waste materials, especially chemical waste. Whether motivated by a desire to avoid adverse affects to the environment, or simply to comply with the numerous laws and regulations affecting waste disposal, chemical users of every description have become increasingly aware of the prohibitions against indiscriminate disposition of waste materials, particularly those containing any reactive chemicals, any solvents, non-biodegradable oils and the like. Various hazards are associated with many waste chemicals, including many chemicals previously thought to be relatively benign from a health or ecology standpoint.

As the ability of chemical manufacturers to modify simple oils, solvents and other reagents to assist them dispersing other liquids and solids within them has increased, whereby a great variety of materials, particularly liquids and finely subdivided solids are emulsified, coupled or rendered soluble within a solvent or external phase carrier, the potential for transporting diluted materials to unattended or uncontrolled disposal sites has increased greatly. Consequently, in many modern industrial processes, waste materials are generated which are toxic, dangerous or undesirable simply because they have small quantities of toxic materials disposed within what might otherwise be an innocuous material. Many materials, while not toxic at a particular time, may be converted into toxic wastes or may be leached out of inert or benign carriers. Of course, some solvents and other chemicals create waste disposal problems per se.

However, as concern with disposal has grown, an industry has emerged which is devoted to safe disposition of chemical wastes of various kinds. The basic premise for safe disposition of dangerous or questionable chemicals is that, once the product to be disposed of is identified, the nature of the risk it holds out can be assessed and proper steps may be taken to dispose of the chemical. From a theoretical standpoint, this approach is sound and serves as a basis for most, if not all, commercial chemical waste and disposal operations. However, practical problems of achieving chemical waste disposal remain substantial, and remain in need of continually improved approached to make headway in safe disposal practices. Many of these problems are then able to be overcome, when the nature of the product to be disposed of is fully understood.

Through ignorance or mistake, if the presence of a harmful material is unknown or is overlooked, the potential for an improper disposition method, and hence downstream environmental damage is greatly magnified. In other words, the more likely it is that the waste disposer is unaware of the nature of the material to be disposed of, the more likely it is that a proper disposition will not result.

As a consequence of the foregoing situation, there have been on-going requirements for waste disposers and/or recyclers to analyze waste stream materials to ensure that such materials are in fact as they are represented to be by the generators thereof. If materials inbound to a licensed disposer are of an unknown character, they will require detailed analysis. Consequently, although there has been a great increase in the technical ability of waste disposers and recyclers to analyze incoming materials, particularly liquids, sampling procedures for the incoming materials can themselves be the subject of mistakes and errors, as well as a source of unduly high cost. By way of example, with incoming waste being readily able to be analyzed on the basis of parts per million, and in many cases, industrial instrumentation being capable of identifying contaminants present in only parts per billion quantities, it is essential that the sampling process itself not only be done economically and reliably, but that it does not become a source of error in and of itself.

Thus, in the case of a drum of inbound liquid waste, for example, it is necessary for analysis that a representative sample of the material be taken. This implies that, particularly if there are materials of various densities present within a single container, that a sample be taken which accurately represents the entire material, i.e., that the sample contains elements from top to bottom of the container. In other words, the sample taken should replicate as closely as possible the exact make-up of the material being sampled.

If a sampling device is used repeatedly, it is necessary then either to clean the device after each use to avoid contamination by way of "carry over" or cross-contamination. Often, the cleaning process involved the use of solvents, aqueous emulsifiers or the like and this can lead to a false reading in one or more successive sampling operations. Therefore, it would be desirable to have a sampling device which would be manufactured economically enough to be thrown away after one use, or which could at least be made of relatively inert materials and capable of reliable cleaning without compromising performance.

It would also be desirable to have a sampling device, which although made from a low cost material, would still be highly reliable and potentially accurate in use.

In addition to having the foregoing characteristics, a sampling device should be one which is fool-proof in use and which permits accurate replication of the container contents during the sampling process. According to the present invention, this is achieved by providing a sampling device including a retention tube, a tube plug unit, and an operating rod and handle, with the tube being simple and economical and the plug and operating rod and handle being arranged to perform the multiple functions of sample gathering and retention in an extremely reliable manner at low cost.

In view of the failure of the prior art to provide a reliable, low cost sampling device, particularly for withdrawing liquid specimens from drums or other containers, it is an object of the present invention to provide an improved, low cost sampling device for liquids and the like received in shipping or storage containers and desired to be analyzed before shipment or treatment.

Another object of the invention is to provide a low cost sampling device which includes three extremely simple, low cost components including a retention tube, a multi-function plug unit and a multi-function operating rod and handle unit.

Still another object of the invention is to provide a sampling apparatus which may be made in a variety of sizes, particularly length, and thus be adapted to sample fluids within a variety of container sizes and styles by varying only the length of the tube and the rod and handle unit.

Yet another object of the invention is to provide an apparatus which may be inserted into the plug-receiving opening of a liquid containing drum or the like with the plug adjacent but spaced from the tube end, lowered to a desired depth while keeping the lower tube end open and then, by using a built-in gauging system comprising a novel arrangement of the rod and handle, capture a sample by moving the rod slightly to ensure that the tube is closed and the sample is trapped therein without disturbing the representative character of the sample.

A further object of the invention is to provide a sampling device wherein the plug unit includes a receiver for the lower end of the operating rod, a transverse plug head portion, a peripheral plug skirt with a tapered skirt seal, and wherein the plug head is supported by tapered ribs or the like serving as pilot surfaces for guiding the plug into the open end of the tube and closing off the lower tube end.

A still further object of the invention is to provide a multi-position engaging arrangement between the upper end of the operating rod and handle and the upper tube end, by providing a curl and transverse section of the rod end, with the transverse section being offset from the rod shank whereby the transverse portion may rest atop the tube end in one end position and whereby the tube end may engage a portion of the curl in another plug position.

Another object of the invention is to provide a sampling system wherein the retention tube is made simply from a length of polypropylene or other chemically inert plastic tubing and wherein the other components are also made at low cost.

A still further object of the invention is to provide an arrangement as described wherein a fine or vernier adjustment of the plug position relative to the rod may be achieved in a simple manner.

An additional object is to provide a sampling device which inherently reproduces a specimen which is representative of the liquid in which the tube is immersed, inasmuch as the tube is designed to extend from a position adjacent the top to a position in contract with or very near the bottom of the container.

A still further object of the invention is to provide a device wherein the portion of the plug may also be used to contact or sample sludge or other materials lying at the bottom of the drum or other container being sampled, or to exclude such materials from the sample-taking process.

The foregoing and other objects and advantages of the invention are achieved in practice by providing a sampling device including a hollow sample retention tube with open top and bottom ends, an operating rod and handle terminating at its upper end in a loop or curl and a transverse end portion for respective engagement with an edge of the upper tube and having attached at its lower end to a plug body having a head, a skirt, a peripheral seal for the skirt, and plural tapered support ribs extending from one part of the plug body to the radially outer portions of the plug head and serving as pilot surfaces for guiding the plug end into a desired position within the tube interior.

The manner in which the foregoing and other objects and advantages are achieved in practice will become more clearly apparent when reference is made to the following detailed description of the preferred embodiments of the inventions set forth by way of example and shown in the accompanying drawings wherein like reference numbers indicate corresponding parts throughout.

BRIEF DESCRIPTION OF THE DRAWINGS

FIG. 1 is a side elevational view, with portions broken away, from a waste drum filled with liquid and showing the sampling device of the invention being inserted into the drum;

FIG. 2 is a side elevational view, with portions broken away, showing the fluid sampling device of the invention in one position of use;

FIG. 3 is a view similar to that of FIG. 2 but showing the sampling device in another operative position;

FIG. 4 is a fragmentary view of the top portion of the sampling device of FIGS. 2 and 3, taken along lines 4—4 of FIG. 3;

FIGS. 5A and 5B are elevational/sectional views of the sampling device of the present invention, showing the same in the process of obtaining a specimen from a drum filled only with liquid;

FIGS. 6A, 6B and 6C are diagrammatic views similar to those of FIGS. 5A and 5B, showing the collection of a specimen of sludge from a sludge cake resting on the bottom of a container whose liquid contents are also to be sampled;

FIG. 7 is a view, partly in elevation and with portions broken away, showing certain constructional details of the head portion of the sampling device of the invention.

DESCRIPTION OF THE PREFERRED EMBODIMENTS OF THE INVENTION

While the present invention may be embodied in different forms, and may have some of its components made from different materials and by different methods, a description of a preferred form of the invention will be given wherein the components are relatively inert plastic materials and an aluminum alloy or the like, and are made by known techniques intended to achieve maximum economy of manufacture consistent with reliable performance in use.

Referring now to the drawings in greater detail, FIG. 1 shows the sampling apparatus of the invention generally designated 10 to be embodied in a unit for sampling the contents, generally designated 12, of a drum or like receptacle generally designated 14. Preferably, the drum 14 will included a head or cover 16 having an access opening 18 therein defined by a fitting 20 from which a cover seal or plug (not shown) has been removed. The contents 12 of the drum 14 may include a liquid, supernatant layer 22 suspended above a "sludge cake" or semi-solid bottom layer 24, resting on the upper surface 26 of the container bottom wall 27.

While it is not necessary that the container have such contents, for purposes of illustration, it is assumed that the container will contain either all liquid material or, in the alternative, a liquid disposed above a solid or semi-solid layer of caked sludge at the bottom thereof. Inasmuch as it is a principal object of the invention to provide an accurate, reliable sample of the contents of the container, including a sample reflecting the various strata, if any, of the liquid 22 forming the contents 12, the sampling apparatus 10 is constructed and arranged as will be described. Referring now to FIGS. 2 and 3, the sampling apparatus 10 includes three principal elements, a retention tube generally designated 28, an operating rod generally designated 30, and a remotely positionable bottom seal plug unit generally designated 32 for closing off the bottom end of the tube 28.

The retention tube 28 includes an upper, open end generally designated 34 defined by a circular top edge surface 36, a thin, cylindrical side wall 38, and a lower tube margin 40, beneath which is a cylindrical edge 42 defining a tube bottom opening generally designated 44 of circular cross-section. The inside diameter surface 46 of the retention tube 28 is also cylindrical in shape and has a smooth surface finish to provide the potential for the effective sealing action to be described. The retention tube 28 is preferably made from a naturally lubricous plastic material that is inert to most chemicals. One such preferred material is polypropylene.

The second component of the apparatus 10 is the operating rod generally designated 30, which includes an elongated shank portion 48, an upper or loop end portion generally designated 50 (FIG. 3). The loop portion 50 includes a transverse end section 52 that extends horizontally in its normal position of use, and forms the end of a 270 degree curl section 54, which begins at the upper or vertical end of the shank 48 and curls about until its transverse end section 52 lies in a substantially horizontal plane. In the curl area 54, there is a radial offset 39 (FIG. 4) between the axis of the shank 48 and the axis of transverse rod end 52, for reasons which will appear.

The lower portion of the rod shank 48 includes a threaded section 56 (FIG. 7) which is the preferred manner of attaching it to the third principal element, namely the remotely positionable plug unit 32.

Referring now in greater detail to the plug unit 32, this element is shown (FIGS. 2, 3 and 7) to include a plug body generally designated 58, including a cylindrical center core 60 having a longitudinal bore 62 which, as formed, is free of threads. However, when the threaded lower end portion 56 of the operating rod shank 48 is inserted into the bore 62 and rotated, the threads 56 tap or cut threads 64 in the bore 62.

Surrounding the core 60 is a generally cylindrical plug head generally designated 66 and having a slightly cone-shaped or crowned surface 68 formed integrally with and joined to a plurality of generally triangular gussets or ribs 70. By forming the plug upper surface with the crown or taper, it will not retain liquid on its upper surface. The head 66 also includes a cylindrical skirt 72 depending downwardly from the top surface 68 of the head 66; the skirt 72 terminates in an outwardly flared, flexible plug seal 74. For purposes of forming a light but positive seal, there is a preformed or molded interference between the outer diameter of the peripheral seal 74 and the inside diameter surface 46 of the tube 28. Accordingly, a fluid-tight seal is able to be achieved by a light but definite interference between these parts. Preferably, such molded interference, measured on diameters, might be 0.040" to 0.080" in the case of a tube with a 1.5" inside diameter. As is best shown in FIG. 7, a plug extension 77 with a bottom surface 79 is provided to insure that the plug seal is spaced sufficiently upwardly within the lower tube opening that the seal 74 engages the inner sidewall surface 46 of the tube 28.

In the preferred form of apparatus, the plug assembly is molded from a compliant material such as low density polyethylene, and accordingly easily possesses sufficient flexibility to create a fluid-tight seal. Referring in particular to the configuration of the plug head, and particularly to the gussets or ribs 70, it will be noted that their construction, i.e. tapering from a point tangent to the diameter of the skirt 72 to a point adjacent the core 60 of the plug body 58 enables them to serve as guide or pilot surfaces during the time the plug is being guided into the open lower end 44 of the retention tube 28. Naturally, as an alternative, the entire top surface could comprise a steep cone, which would combine the drainage and pilot features.

Referring now to the operation of the apparatus, there are three basic conditions under which samples are desired to be taken. Thus, the apparatus is suitable for obtaining a liquid-only sample, from the drum, whether or not there is a sludge layer or cake beneath the liquid. In another case, where there is a sludge layer, it may be desired to obtain a specimen of both the sludge layer and the supernatant liquid. The apparatus of the invention readily accomplishes this purpose.

A third circumstance arises where there is sludge in the form of a semi-solid or solid layer resting on the bottom of the drum, and it is desired to obtain a specimen of this solid or semi-solid layer without the liquid. The same apparatus can collect these three kinds of samples, depending on the contents of the container and the manner in which the sampling apparatus is manipulated.

In connection with visualizing the manner of obtaining the first kind of specimen, i.e., liquid only, reference is made to FIGS. 2, 3, and FIGS. 5A and 5B of the drawings. Referring to FIG. 2, it will be noted that the length of the rod 28 is what limits the extent to which the plug 32 will extend downwardly beneath the lower rim or edge 42 of the tube 28. Thus, the lowermost surface 76 of the top of the curl 50 of the operating rod 30 is arranged, together with rod length and the arrangement of the plug core 60, to precisely position the plug 32.

Thus, when the upper edge 34 of the tube 28 engages the curl surface 76, only the top of the plug core 60 lies inside the retention tube 28. In other words, the shoulder between the rod shank 48 and the plug core 60 still lies above the bottom edge 42 of the tube 28. When the operating rod is lifted or pushed vertically, therefore, the lower, cylindrical edge 42 of the retention tube 28 engages one or more of the tapered or beveled edges of the gussets or ribs 70, creating a guiding or self-centering, "pilot" action as the plug moves into the opening 44. As the plug 32 continues to move upwardly relative to the tube, the surfaces guide the plug in such a way that there is initial engagement between the skirt 72 of the head and ultimately, between the plug seal 74 and the inner diameter surface 46 of the tube 28. By pushing the tube fully toward the bottom of the drum, such that the bottom tube edge 42 touches the bottom 26 of the drum, the plug extension 77 will also have engaged the drum bottom 26, thus moving the plug 32 far enough up in the tube 28 to insure that the plug seal 74 lies within and engages the tube wall 46.

When the operating rod has been lifted or pushed to an extent wherein the peripheral seal 74 lies well within, but not unduly upwardly of the bottom edge 42, the end section 52 is moved sideways to the position of FIG. 4. Then the transverse or horizontal end section 52 of the operating rod 30 will rest atop the open, upper end 34 of the retention tube 28. The corresponding amount of plug movement will capture and retain whatever liquids lie within the tube interior and above the plug head. Assuming this to have occurred when the tube is within the container, the entire column of liquid will then be trapped for subsequent transfer to a shipment, storage and/or analysis vehicle. To discharge the tube contents, when the lower tube end is disposed within the mouth of a storage or analysis container, the operating rod is simply moved sideways such that the transverse end no longer engages the upper end of the tube and operating rod is simply pushed downwardly, opening the bottom end of the tube and allowing the contents to flow out of the tube. The crowned plug top surface unsures that the entire contents drains out.

FIG. 3 shows such a position of the operating rod and plug relative to each other. The exactly desired dimensional relationship can be insured by rotating the operating rod relative to the plug to cause the threaded shank to cut threads into the bore 62 on the plug core 60 to a greater or less extent.

Referring now to FIGS. 5A and 5B, the operation of the device is shown in relation to a container generally designated 14a wherein the contents 22a are entirely liquid. Here, as shown in FIG. 5A, the entire tube is inserted into the drum opening and the tube lower end is moved to a position adjacent the bottom surface 26a of the drum. When the lowermost surface 79 of the plug extension 77 contacts the lower drum surface 26, the lower edge 42 of the tube 28 is spaced well apart from the plug, leaving the opening 44 in the tube bottom fully open. Because of gravity, therefore, the liquid will have filled the tube fully. Assuming that the liquid is stratified, and it is desired to replicate the stratification within the sample tube, i.e., not unduly disturb contents, the sampling apparatus 10 is lowered gradually and easily into the drum, and collection of a stratified specimen will result.

Referring now to FIG. 5B, the directional arrow shows that, the plug extension 77 having been in contact with the bottom 26a of the drum 14a, downward tube movement will be necessary to trap the liquid sample. Here, the operator continues to push the tube 28 downwardly until the lower edge 42 of the retention tube 28 engages the bottom of the drum. At this point, a specimen has been trapped and the plug is received within and sealed relative to the tube 28. The top of the rod is moved sideways to the position of FIG. 4, locking the rod against unintentional movement. Thereafter, simply lifting the tube 28 without moving the plug 32 withdraws a liquid sample for transfer into a shipping or sampling vessel. The simple expedient of pushing the operating rod sideways and down and permits the contents to flow from the bottom of the tube.

Referring now to FIGS. 6A–6C, there is shown a similar but slightly different method. Here, it is desired to obtain a liquid specimen as well as a specimen of the sludge cake 24 lying beneath the liquid contents of the drum.

In FIG. 6A, a drum generally designated 14b is shown to have a layer or cake of sludge 24 lying on its lower surface 26b. The remainder of the contents constitute a liquid material 22b. In FIG. 6, it will be noted that in the initial position, the plug 32 or plug extension 77 rests atop the generally solid or semi-solid sludge cake 24. Thus, when the tube and plug are gradually moved downwardly, the engagement between the plug and the sludge cake will be felt by the operator. As the tube continues to move downwardly, the operating rod will cease to move. During the initial phase, as shown in FIG. 6A, the bottom opening 44 of the tube 30 remains unobstructed and the plug is resting on the sludge cake. Continued downward movement of the retention tube 28, as shown in FIG. 6, is achieved by holding the operating rod in a fixed position and gradually moving the tube to the position shown in FIG. 6B. As the bottom margin 40 of the tube 28 closes over the lower portions of the skirt and seal 72, 74, the liquid contents are trapped in the tube above the plug, as shown in FIG. 6B.

Further according to the invention, when it is also desired to withdraw specimen of the sludge cake, this is done by simply continuing downward movement of the tube 28 relative to the sludge cake and relative to the plug. As shown in FIG. 6, the lower margin 40 of the tube, in effect, cuts a core sample or cylindrical plug of sludge from the cake. The sample remains embedded in the cylindrical lower opening beneath the plug but above the bottom surface 26b of the drum. At this stage, when the operator feels positive interference between the lower edge 42 of the tube and drum bottom surface 26b, the entire apparatus is slowly lifted up and withdrawn from the container.

Here, the operator may deposit the plug or core taken from the sludge cake within its own analysis or storage vessel by moving the plug 32 downwardly to the extent sufficient to discharge only the plug. If it is desired to analyze the contents of the liquid separately from those of the sludge cake, the lower end of the tube 28 is then positioned within the mouth or interior of another vessel and the operating rod is manipulated so as to push the plug out the open bottom end of the tube, permitting the liquid contents entrapped in the tube to flow into the vessel.

Referring now to the third form of sampling, i.e., obtaining a core specimen of sludge only, this is easily done. Here, the plug 32 is prepositioned as shown in FIG. 3, so that it closes off the bottom end of the tube 28. In order to take a specimen of the sludge cake only, the apparatus 10 is then inserted into the drum. When the bottom edge 42 of the tube 28 engages the sludge cake 24, the apparatus will be in a position such as that shown in FIG. 6B, except that the tube interior will be empty and free of liquid.

Next, the tube itself is simply moved down, as is shown in FIG. 6C, thus cutting a core or plug specimen from the sludge cake. The apparatus as a whole is then removed from the drum and the sludge cake transferred to an appropriate vessel as just described.

According to the invention, by making the apparatus from the described materials, a very inexpensive sampling apparatus can be made. Regarding the construction of the operating rod, while a number of materials are suitable, a presently preferred form of the invention uses a thin aluminum alloy rod, preferably of a 0.213" diameter and made from a 5000 series aluminum alloy, such as a 5056-H32 grade alloy. Roll-formed threads are imparted to the lower rod end, with such operation enlarging the outside diameter portion of the rod thread to about 0.250". The roll-formed threads are still sharp-edged enough to be self-tapering with respect to the plug core 60. After the other rod end is curled as shown in FIGS. 3 and 4, the rod has sufficient strength and flexibility to function satisfactorily in its intended environment.

The importance of sampling the contents of collected industrial waste is achieving ever greater recognition in environmentally responsible countries. The present invention provides a simple and effective way to permit drums or like containers of such liquids to be sampled so that an appropriate manner of disposition or recycling can be determined without necessitating a prior shipment of the drums.

The reasons for this are several. First, before drums are shipped, the nature of their contents should be determined so that appropriate safeguards may be taken. It may be possible, depending on the character of the waste, to dispose of part of the drum contents on site and to dispose of the remainder in another way. In other cases, where the contents are relatively benign, and/or contain value from a recycling standpoint, shipment or transfer of the whole drum to a particular destination may be indicated. Thus, the concept of waste concentration and minimization may be followed.

It is of great concern that an accurate analysis of industrial waste content be made at the earliest possible time, and the present invention provides an economical and reliable manner of achieving the foregoing and other objects. A typical analysis includes, but is not limited to a so-called TCLP (Toxicity Characteristics Leaching Procedure) Analysis. Other tests are indicated for waste oils, hazardous wastes generally, including, but not limited to, metals, pesticides, etc.

A preferred embodiment of the invention having been described by way of example, it is anticipated that other variations and changes to the described form of apparatus may occur to those skilled in the art and it is anticipated that such modifications and changes may be made without departing from the spirit of the invention or the scope of the appended claims.

I claim:

1. An apparatus for sampling liquids in containers, said apparatus comprising, in combination, a sample retention tube, a tube plug unit, and an operating rod and handle unit, said retention tube being of a cylindrical cross-section and having a continuous thin sidewall made from a thermoplastic material, said tube having completely open, top and bottom end portions, said tube plug body including a rod-receiving, center section and a plug unit having a generally upwardly directed top surface and a peripheral seal extending radially outwardly from a lower portion of said plug body, said seal being adapted to sealingly engage an inner surface of said tube sidewall, said operating rod having a main section, a lower end and having its handle at the top of said rod, said rod having an overall length in excess of that of the retention tube and having said lower end portion received snugly within said plug center section, said handle including a loop portion at its upper end, with said loop portion terminating in a transverse section, with said loop portion also being inclined relative to the axis of said rod main section, whereby said transverse end section is spaced apart from an adjacent portion of said rod main section by a distance substantially greater than the thickness of said tubing wall, said tubing top end portion being engageable with said transverse end section of said rod in one position of said rod handle, and with the uppermost portion of said loop end engaging said tubing top end portion in another position of said rod, and with said rod length and loop size being arranged such that, with said transverse end in contact with said top tube end, said entire tube plug unit is disposed within said retention tube, and with said top tube end engaging said upper loop portion, said plug is sufficiently spaced from said bottom tube end to permit the liquid to be sampled to flow into said bottom tube end.

2. An apparatus as defined in claim 1 wherein said retention tube is made from a polyproplyene material.

3. An apparatus as defined in claim 1 wherein said tube plug unit is made from a low density polyethylene material.

4. An apparatus as defined in claim 1 wherein said upwardly directed top surface of said plug unit is a slightly tapered crown surface and wherein said plug unit further includes plural tapered guide surfaces extending from said plug crown surface to said plug center section.

5. An apparatus as defined in claim 1 wherein said lower end of said operating rod includes a threaded end portion, with said center section of said plug being a cylindrical section having cooperating thread portions formed therein and cut by said threaded rod end, whereby said snug reception between parts comprises an adjustable, threaded connection.

6. An apparatus as defined in claim 1 wherein the inside diameter of said retention tube is from about 1 inch to about 2 inches.

7. An improved three-element sampling device adapted for economical manufacture and able to be discarded after a single use, said sampling device being intended for use in removing samples of liquid products from drums, barrels, or the like, said sampling device comprising, in combination, a retention tube, said retention tube having open top and bottom ends each terminating in margins having edges of substantially circular configuration, and a combination operating rod and tube plug unit, said operating rod having a lower end portion adapted for snug reception within a portion of said plug and an upper end portion including an axially extending shank, a curl portion and an end portion extending horizontally, with said horizontally extending end portion being offset from the outer surface of said rod shank by at least the thickness of said tube wall, whereby said transverse rod end rests upon said upper tube edge in one position of said rod and whereby said rod, in another position, is supported by engagement between said upper tube edge and a portion of said rod end curl, said tube plug including a plug body with a central rod end-receiving section of generally cylindrical shape and having an upper end face, and a cylindrical skirt terminating at its lower edge in a plug skirt seal element, with said plug head also having plural tapered guide surfaces extending upwardly and inwardly from the outer margin of said plug upper end face and toward said rod, with said rod being of such length that, with said plug attached thereto and said horizontal rod end engaging said tube upper surface, said plug skirt and seal lie within and are surrounded by the lower margin of said retention tube, and whereby, with said upper tube edge engaging said rod curl, said plug extends below said lower tube margin to provide an opening between said lower tube end margin and said plug unit to permit fluid to flow into said retention tube for sampling.

8. An improved sampling device as defined in claim 7 wherein said retention tube is made from a thermoplastic material that relatively inert to chemical solvents wherein said plug is also made from a thermoplastic material.

9. An improved sampling device as defined in claim 7 wherein said tube is made from polypropylene and said plug is made from a low density polyethylene material.

10. An apparatus as defined in claim 1 wherein said transverse end section of said handle intersects said upper end portion of said rod at a distance of from about 1 inch to about 2 inches from said uppermost portion of said rod loop.

* * * * *

UNITED STATES PATENT AND TRADEMARK OFFICE
CERTIFICATE OF CORRECTION

PATENT NO. : 5,445,038
DATED : Aug. 29, 1995
INVENTOR(S) : Theodore H. Hueller

It is certified that error appears in the above-indentified patent and that said Letters Patent is hereby corrected as shown below:

On title page, item [19] "Hueller" should read —Hueller, et al—
           item [75] "Theodore H. Hueller, Cary, Ill." should read
—Theodore H. Hueller, Cary, and Bruce A. Blair, Sycamore, all of Ill.—

Signed and Sealed this

Thirty-first Day of October 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,445,038

DATED : Aug. 29, 1995

INVENTOR(S) : Theodore H. Mueller

It is certified that error appears in the above-indentified patent and that said Letters Patent is hereby corrected as shown below:

On the title page, item [19] "Hueller" should read --Mueller, et al--; and item [75] "Theodore H. Hueller, Gary, Ill." should read --Theodore H. Mueller, Gary; Bruce A. Blaire, Sycamore, both of Ill.--.

This certificate supersedes Certificate of Correction issued October 31, 1995.

Signed and Sealed this

Fifth Day of December, 1995

Attest:

Attesting Officer

BRUCE LEHMAN

Commissioner of Patents and Trademarks